May 5, 1953 J. D. BROWNELL Plant Pat. 1,182
ROSE PLANT
Filed Jan. 31, 1952
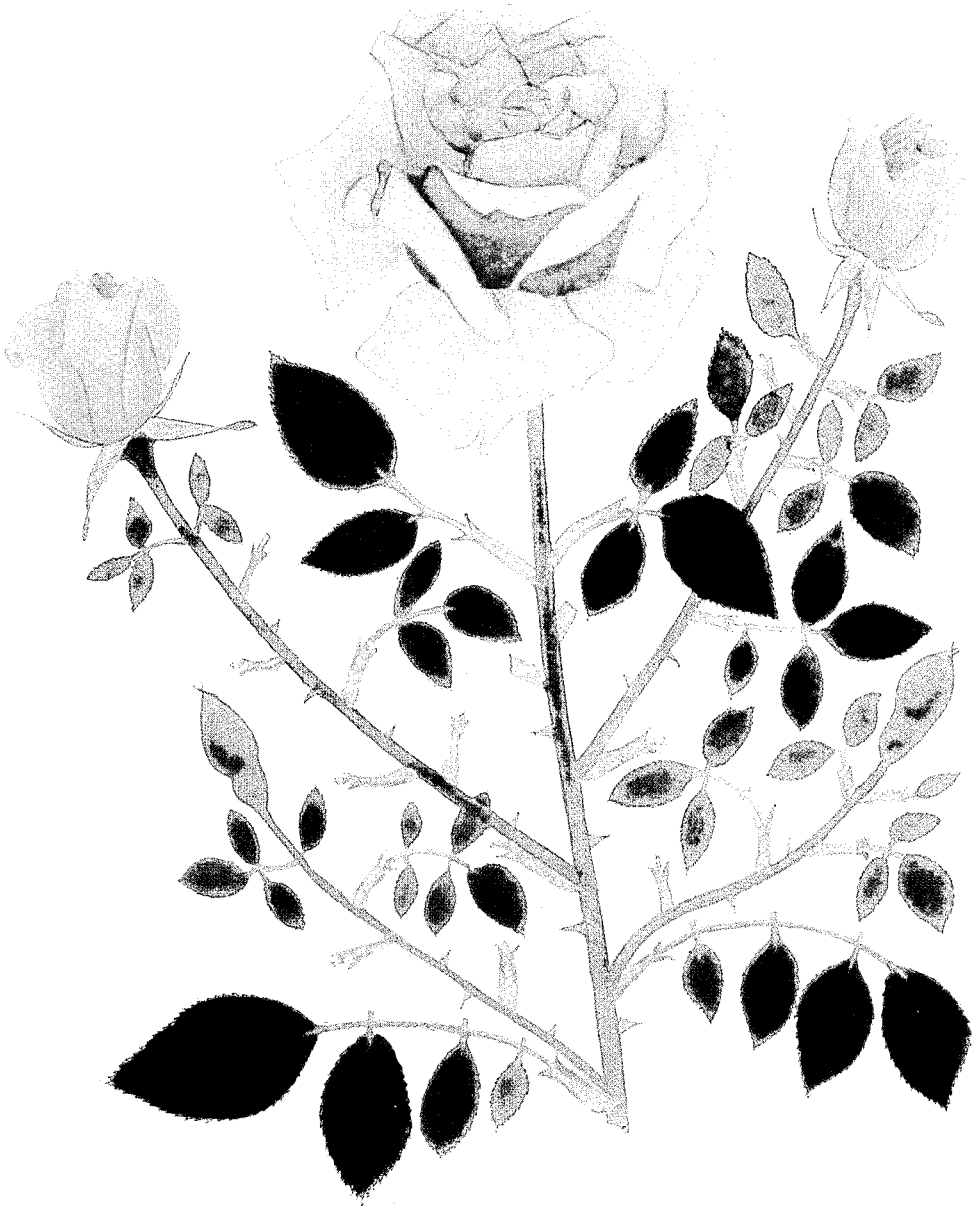
INVENTOR.
Josephine D. Brownell.

Patented May 5, 1953

Plant Pat. 1,182

UNITED STATES PATENT OFFICE 1,182

ROSE PLANT

Josephine D. Brownell, Little Compton, R. I.

Application January 31, 1952, Serial No. 269,255

1 Claim. (Cl. 47—61)

My invention relates to rose plants and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States:

The deep red shades (ordinary dictionary definition) of its petals, in combination with the unique brilliance thereof and their tendency to hold these colors under exposure;

The novelty and variation within certain definite limits of the form of the bloom, its character of holding that form for a long time, and the petallage of the flowers;

Its character of fragrance;

Its unusual abundance of flowers, notable after early bloom time and until frost;

The intensity of its remontant and everblooming or reblooming character;

Its character of ascending in height by recurrent branching and progressively longer stems from the base;

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

Under the natural conditions of exposure where this rose was grown it has shown some resistance to black-spot.

In the accompanying drawing forming a part of this specification I have shown my new rose in its natural colors, that is, as near as is possible to do so artificially.

My new rose is otherwise described as follows:

*Essential information*

Type: Hybrid tea, *Rosa wichuraiana* hybrid, dwarf to ascending, for garden display, cut flower and forcing or growing under glass.

Class: Hybrid tea crossed with *Rosa wichuraiana*, further restricted by originator to include only those varieties that can survive moderately low sub-zero temperatures.

Breeding: This variety was produced and bred by me and under my direction by propagation and cross pollenation.

It came into being as a seedling grown from a seed borne on a plant which was a seedling with seed parent "Pink Princess" Plant Patent No. 459, pollen parent "Mirandy" Plant Patent No. 632; and the pollen parent was "Queen o' the Lakes" Plant Patent No. 1003, both parents having been produced by me and under my direction.

The pollenation that fertilized the seed that grew into my new rose, as well as the two previous pollenations that produced the two parents of my new rose, were directed by me and were performed by emasculating flowers and placing thereon a bag protecting from self and foreign pollen. These bags were later removed and the flowers were hand pollenated with a camel's hair brush and the bags immediately replaced. The date of the pollenation of my new rose was July 2, 1950.[1] The seed was planted for me and under my direction on December 24, 1950, and the date of the first flower was July 24, 1951.

I have since made and directed extensive propagations and tests of this plant and flower.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1951 inclusive and the characters have successively reproduced, true to the original seedling.

*Flower*

Habit: It blooms out of doors in Little Compton, beginning about three days prior to the average beginning time of commercial hybrid teas and continues relative to growth of the plant until frost.

Flowers borne: Often one, frequently two or three and occasionally more on each stem, in the usual hybrid tea type of cluster and in the polyantha type of cluster occasionally in a raceme nearly half way down the longer stems. The pedicels and peduncles are medium in diameter and medium in length, erect, stiff, almost smooth, free from large prickles and bristles but with a few very small prickles varying to small hairs. Stems are long, medium to small in diameter, and notably stiff and rigid.

Quantity of bloom: Free, being cumulative in quantity from year to year as the plant increases in size, flowering through the summer and fall.

Fragrance: Distinctive, pleasing China tea in combination with that of *Rosa wichuraiana*, under favorable environment.

Bud: Neck normal as described, opens well, being little to not at all affected by hot or wet weather

[1] This and other dates herein are approximate.

or both, as to color and form, except at very high temperatures the color is less intense and the form of the petals is less recurled.

Before the calyx breaks the size is medium, form high centered, frequently with one or more sepals having foliaceous parts extending beyond the apex of the calyx up to about three quarters of an inch, the number and size of the foliaceous parts being variable and rarely having one or more narrow, pointed, minutely serrate appendages on each side of the sepals, otherwise the sepals are usually normal and regular, tapering to lanceolate at their apex, turning back nearly perpendicular to the pedicel as the bud opens.

Color of the bud as the calyx opens, Cardinal Red at 822 shading to nearly Orient Red in 819; color reference to English Horticultural Color Chart.[1]

Bloom: As the bud opens and the flower develops to maturity the color outside of petals slowly changes toward Crimson at 22 at maturity. Inner side Cardinal Red at 822 variously shading to Turkey Red at 721/3; holding color unusually well in bright sunlight slowly softening toward Crimson at 22.

The flower usually varies in size between four inches and five inches in diameter when fully open, occasionally larger, petals average around 45, frequently some smaller petals and petaloids in the center, variable in number.

The flower opens high centered, formal, recurled, with late display of stamens and pistils. The petals are variable from obovate to ovate to irregular and frequently with surfaces variously warped and edges especially of the smaller petals frequently notably irregular. Texture is medium to thick and leathery; both sides brilliant with slight veining which is not prominent. The time of opening under favorable conditions is four to five days.

The pedals are substantial and after about five to six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

Reproductive organs:

Stamens, quantity variable, medium long, of slightly uneven length.

Anthers, nearly Marigold Orange at 11/3. Filaments, nearly Tangerine Orange at 9/3.

Pistils are several of slightly uneven length, averaging about one-half inch long.

Ovaries are usually all inclosed.

Sepals are persistent and break off easily.

*Plant*

Foliage: Is abundant, of compound leaves of three to five leaflets near the flower, five leaflets lower down the stem and frequently seven leaflets in the middle of the stem and nearer the base. Size of leaflets medium, averaging in size a little larger than half way between the average hybrid tea and the *Rosa wichuraiana* leaflets. As the plants develop in size some of the leaflets develop to nearly twice the size described above. Form of leaflets usually ovate with apex moderately acute, base rounded to semi-pointed, in some instances with the circumference on one side of the petiolule out of alignment with the other side by about one-sixteenth of an inch or less, margins with slightly irregular small pointed serrations, petiolules short.

[1] Color references to same unless otherwise indicated.

The leaflets average in width about one-half to two-thirds of their length.

Color of leaflets on the upper surface is slightly variable from Scheeles Green at 860, irregularly shaded with Spinach Green at o960/1, with reverse side nearly Asphodel Green frequently overlaid with trace of Dahlia Carmine, the last two color references are to Robert Ridgway Color Standards.

The rachises are medium, moderately narrow to slender, upper side smooth except some very short hairs on edge. Under side moderately smooth, usually 3 to 5 short prickles.

Stipules are medium to long, averaging about three-quarters of an inch long, with sharp points, the upper edges of which normally form an angle of about 90 degrees.

Habit, dwarf, becoming bushy to tall; upright, compact, more cumulative in growth from year to year than the normal hybrid tea rose plant, by stems from the base and by rebranching and growth and enlargement and extension of the stems from the base. The growth is moderately free at first, developing more rapidly after one or two years under favorable vegetative opportunity.

Color of mature stems is Scheeles Green at 860/3, shading variously lighter and also occasionally with slight overlay of Spinel Red at oo23/1 variable in intensity, usually more pronounced on the sunny side.

Prickles, several, frequently two to four between leaves, averaging in length about one-quarter inch, shading from Crimson at 22 to lighter at the base, turning lighter throughout and later to nearly colorless. Hairs few on upper portions of stems.

Winter resistance: A notable characteristic of this new rose is the resistance to moderate sub-zero temperatures in combination with its hybrid tea character and its *Rosa wichuraiana* ancestry. This variety with grafted bud and plant above that bud, entirely exposed above ground to moderate sub-zero temperatures survived and bloomed normally the following season. The word "temperature" herein refers to the Fahrenheit scale.

Comparisons: In color my new rose is comparable with that of "Henry Field" Plant Patent No. 841. My rose is much deeper in color, more brilliant, holds its color longer and the color averages more on the yellow side of the spectrum. It branches more and blooms more, and more constantly; and its bloom pattern is more branching as shown.

As compared with "Queen o' the Lakes" Plant Patent No. 1003, it is more brilliant, recurls tighter, and the color averages more on the yellow side of spectrum Red, and its bloom pattern is more branching as shown.

I claim:

The new and distinct variety of rose plant as described and illustrated, characterized by its bloom and color pattern, form and color and its wichuraiana traits.

JOSEPHINE D. BROWNELL.

No references cited.